US012793842B2

(12) United States Patent
Sandor

(10) Patent No.: US 12,793,842 B2
(45) Date of Patent: Nov. 10, 2026

(54) MOBILE TELEHEALTH SYSTEM AND METHOD

(71) Applicant: Goodcheckup Corporation, Naples, FL (US)

(72) Inventor: Marilyn Sandor, Naples, FL (US)

( * ) Notice: Subject to any disclaimer, the term of this patent is extended or adjusted under 35 U.S.C. 154(b) by 720 days.

(21) Appl. No.: 17/726,701

(22) Filed: Apr. 22, 2022

(65) Prior Publication Data

US 2022/0384032 A1 Dec. 1, 2022

Related U.S. Application Data

(60) Provisional application No. 63/286,162, filed on Dec. 6, 2021, provisional application No. 63/192,797, filed on May 25, 2021.

(51) Int. Cl.

| | |
|---|---|
| ***G16H 40/67*** | (2018.01) |
| ***G01J 3/50*** | (2006.01) |
| ***G06T 7/00*** | (2017.01) |
| ***G16H 10/60*** | (2018.01) |
| ***G16H 30/40*** | (2018.01) |

(52) U.S. Cl.

CPC .............. *G16H 40/67* (2018.01); *G01J 3/508* (2013.01); *G06T 7/0014* (2013.01); *G16H 10/60* (2018.01); *G16H 30/40* (2018.01); *G06T 2207/30036* (2013.01)

(58) Field of Classification Search

CPC ....... A61B 5/0088; A61B 1/24; A61B 5/0534; A61B 5/1178; A61B 5/228; A61B 5/742; A61B 5/7475; A61B 5/0022; A61C 5/44; A61C 19/04; G06T 2207/30036; G06T 7/0014; G16H 40/67; G16H 10/60; G16H 30/40; G16H 40/20; G16H 80/00; G01J 3/508; G01J 3/0264; G01J 3/027

See application file for complete search history.

(56) References Cited

U.S. PATENT DOCUMENTS

| | | | | |
|---|---|---|---|---|
| 11,430,570 B2 * | 8/2022 | Tee | ..................... | G06F 21/6245 |
| 2015/0127381 A1 * | 5/2015 | Vo | .......................... | G16H 40/67 705/3 |
| 2017/0032092 A1 * | 2/2017 | Mink | ................. | G06Q 30/0241 |
| 2020/0398063 A1 * | 12/2020 | DeBates | ................ | G16H 80/00 |

FOREIGN PATENT DOCUMENTS

WO WO-2021236616 A1 * 11/2021 ............. G16H 80/00

OTHER PUBLICATIONS

Author(s): Taylor Title: Home telehealth video conferencing Journal: JMIR [online]. Publication date: 2015. [retrieved on: Nov. 10, 2024 ]. Retrieved from the Internet: < URL:https://mhealth.jmir.org/2015/3/e90> (Year: 2015).*

Irving et al. Using teledentistry in clinical practice as an enabler to improve access to clinical care: A qualitative systematic review. 2017.*

Park et al. Implementation of teledentistry for orthodontic practices. Feb. 25, 2021.*

* cited by examiner

*Primary Examiner* — Fonya M Long
(74) *Attorney, Agent, or Firm* — Brennan, Manna & Diamond, LLC

(57) ABSTRACT

A system and methods are used to provide patients access to in-home healthcare, for example, using a device in conjunction with a mobile device. The system and methods described herein are used for tooth whitening applications, general dental or medical checkups, detecting disease, updating dental or medical records, and automatic ordering of prescription and non-prescription products.

10 Claims, 10 Drawing Sheets

MOBILE TELEHEALTH SYSTEM AND METHOD

CROSS-REFERENCE TO RELATED APPLICATIONS

This application claims priority to and the benefit of U.S. Provisional Patent Application Ser. No. 63/192,797, filed May 25, 2021, and U.S. Provisional Patent Application Ser. No. 63/286,162, filed Dec. 6, 2021, the entire disclosures of which are hereby incorporated by reference.

TECHNICAL FIELD

This disclosure relates to systems and methods for mobile telehealth.

BACKGROUND

Independent healthcare providers typically struggle to grow their practices and provide greater access to their patients. One way to grow their practice is to join an established healthcare system. Joining an established healthcare system has several drawbacks. For example, the healthcare provider loses their independence and scheduling flexibility. From the patient perspective, established healthcare systems may provide greater access to a healthcare provider, however, their choices of particular healthcare providers may be limited, particularly in off hours. Accordingly, a system is needed for independent healthcare providers to provide their services to a larger population of patients, provide greater access to care for patients, and maintain their independent practices.

SUMMARY

Disclosed herein are implementations of a mobile telehealth system. In an aspect, a method may include obtaining a patient selection. The patient selection may be obtained via a user interface of a first mobile device. The method may include obtaining an appointment selection. The appointment selection may be obtained via the user interface of the first mobile device. The method may include obtaining a medical history. The medical history may be obtained via the user interface of the first mobile device, and electronic health records (EHR) system, or both. The method may include obtaining payment information. The payment information may be obtained via the user interface of the first mobile device. The method may include transmitting an invitation to a second mobile device in response to obtaining the payment information. The method may include receiving a first notification from the second mobile device. The method may include obtaining a check in. The check in may be obtained via the user interface of the first mobile device. The method may include transmitting a second notification to the second mobile device in response to obtaining the check in. The method may include opening a channel between the first mobile device and the second mobile device. The channel may be a real-time session channel to conduct a telehealth visit.

In an aspect, a method may include automatically populating patient information to generate an electronic prescription. The method may include obtaining prescription information. the prescription information may include a prescribed medication. The prescription information may be obtained via a user interface of a first device. The method may include transmitting the electronic prescription to a pharmacy. The electronic prescription may include the patient information, the prescription information, or both. The method may include transmitting a confirmation that indicates that the transmission of the electronic prescription to the pharmacy is complete.

In an aspect, a method may include receiving data from a device. The method may include displaying the data. The method may include determining a tooth shade based on the data. The method may include obtaining electronic health record (EHR) data. The method may include determining a product. The product may be determined based on the tooth shade, the EHR data, or both.

In an aspect, a method may include receiving data from a device. The method may include displaying the data. The method may include determining tooth decay based on the data. The method may include obtaining electronic health record (EHR) data. The method may include determining a product. The product may be determined based on the tooth decay, the EHR data, or both.

In an aspect, a method may include receiving data from a device. The method may include displaying the data. The method may include determining a disease state based on the data. The method may include obtaining electronic health record (EHR) data. The method may include determining a product. The product may be determined based on the disease state, the EHR data, or both.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Embodiments described herein may allow patients to connect in real-time with a healthcare provider of their choice, for example, through video and/or chat on a mobile device. A healthcare provider may include any medical professional that provides medical, dental, or veterinary services. The system described herein may be used for new patient virtual visits, emergency consultations, and virtual checkups for established patients. The system may allow for the patient and healthcare provider to build a relationship such that the healthcare provider has personalized knowledge of the needs of the patient and the ability to stay connected.

Similar to an in-person visit, the system is configured to obtain the patient history and symptoms, perform a virtual examination, recommend treatment, and prescribe medications. Medical records, dental records, or both, may be uploaded to the system. The system allows for the patient to meet with the healthcare provider in a private space without the stress of a typical office visit. The system may include accessibility features such as magnification and/or visual aids, audio enhancement, or any combination thereof, for creating efficiency and ease of use for patients and healthcare providers with disabilities such as visual or hearing impairment. The system may be configured to perform automatic translations of medical records to that they can be transmitted and viewed on mobile devices to patients and healthcare providers anywhere.

Figure 1:
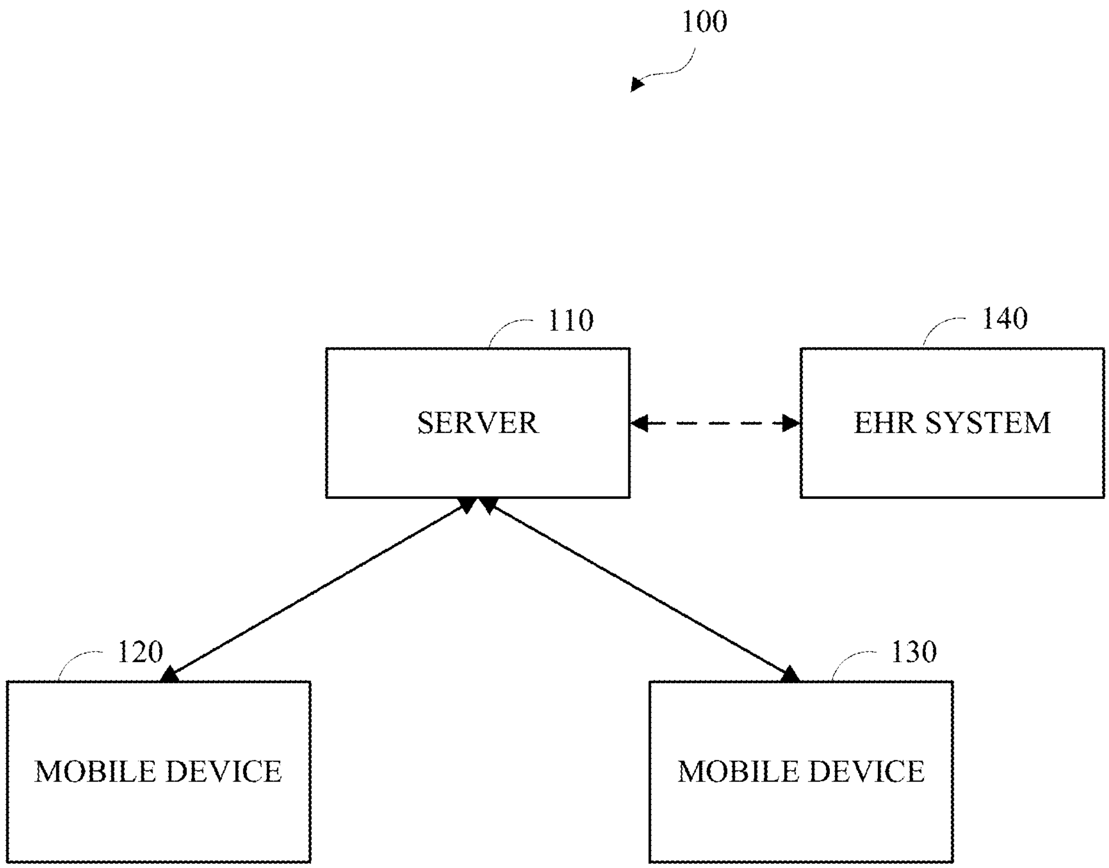
FIG. 1 is a block diagram of an example of a mobile telehealth system.

FIG. 1 is a block diagram of an example of a mobile telehealth system 100. The mobile telehealth system 100 includes a server 110, a mobile device 120, a mobile device 130, and in some embodiments, an electronic health records (EHR) system 140.

The server 110 may be a computer hardware device or software that provides functionality for other programs or devices known as clients. The clients may be mobile devices such as mobile device 120 and mobile device 130. In some examples, the EHR system 140 may be a client. The server 110 may provide services, such as sharing data or resources among multiple clients and devices. The server 110 may perform computations for a client.

In this example, the mobile device 120 may be a patient mobile device and the mobile device 130 may be a healthcare provider mobile device. The mobile device 120 may be configured to run software, such as an application, to communicate with the server 110. The mobile device 130 may be configured to run software, such as an application, to communicate with the server 110. The mobile device 120 may be configured to obtain an existing patient selection or addition of a new patient. The selection or addition of a patient may be obtained via an input on the mobile device 120, such as a touch input or a voice input. The mobile device 120 may be configured to transmit the selection or addition of the patient to the server 110.

The mobile device 120 may be configured to query the server 110 to obtain a list of available appointment slots in a schedule of the healthcare provider. The mobile device 120 may be configured to obtain an appointment selection from the patient. The appointment selection may be obtained via an input on the mobile device 120, such as a touch input or a voice input. The appointment selection may be based on an available appointment slot in the schedule of the healthcare provider stored on the server 110. The mobile device 120 may be configured to transmit the appointment selection to the server 110. The server 110 may receive the appointment selection and update the schedule of the healthcare provider to indicate that the selected appointment is tentative.

The mobile device 120 may be configured to obtain a medical history of the patient. The medical history may be obtained via an input on the mobile device 120, such as a touch input or a voice input. The mobile device 120 may be configured to transmit the medical history to the server 110. In some embodiments, the mobile device 120 may be configured to upload one or more documents and/or images to the server 110. In some embodiments, the server may obtain a medical history or a portion of a medical history from the EHR system 140. The EHR system 140 is associated with the healthcare provider. The EHR system 140 is configured to store electronic health records of patients of the healthcare provider. The EHR system 140 may be located on premises at the office of the healthcare provider, or it may be at a remote location away from the healthcare provider office. In an example, the server 110 may obtain an EHR from the EHR system 140. The server 110 may be configured to receive the medical history or portions of the medical history from the mobile device 120 and the EHR system 140, compile the medical history, and transform the compiled medical history into a unified format. The unified format of the medical history may be stored on the server 110. The unified format may be an alphanumeric format, a visual format, or a combination of both. The unified format is generated using the received inputs to create a labeled map. For example, the dental chart, with the visual representation of teeth is annotated with the information gathered, such as a tooth with decay, chipped tooth, etc. This information may be compiled and unified by placing the information into one document associated with a given patient and stored in the cloud.

The mobile device 120 is configured to obtain payment information. In some embodiments, the payment information can include crypto tokens. The crypto tokens may be Ethereum Request for Comments 20 (ERC-20) or Ethereum Improvement Proposals (EIP-20) tokens. The crypto tokens may be stored on the Ethereum blockchain. The application may include a crypto wallet that allows users to check their crypto token balance and perform supported transactions within the application. The crypto wallets may use Ethereum application programming interfaces (API)s. In an example, crypto tokens may be earned by using certain features of the system, such as watching a video, completing a quiz or tutorial, or the like. In an example, crypto tokens may be awarded for a healthcare achievement, such as a health goal, which can be verified as accomplished within the application. The payment information may be transmitted to the server 110. The server 110 may store the payment information. The server 110 is configured to process the payment and send an invitation to the mobile device 130. The invitation may include information associated with the appointment, for example date, time, type of appointment, patient name, patient symptoms, and any other relevant patient information. The mobile device 120 may be configured to display an indication of the proposed appointment on the display of the mobile device 120. The mobile device 130 is configured to obtain a confirmation from the healthcare provider. The confirmation may be obtained via an input on the mobile device 130, such as a touch input or a voice input. The mobile device 130 may transmit a notification to the server 110. The notification may indicate that the appointment is confirmed.

The server 110 is configured to transmit the notification to the mobile device 120. The mobile device 120 is configured to receive the notification and display an indication of the confirmed appointment on the display of the mobile device 120. The mobile device 120 is configured to obtain a check in from the patient. The check in may indicate that the patient is ready to start the telehealth visit. The check in may be obtained via an input on the mobile device 120, such as a touch input or a voice input. The mobile device 120 may transmit a notification to the server 110 in response to the input. The notification may indicate that the patient is ready to start the telehealth visit. The server 110 is configured to receive the notification and transmit the notification to the mobile device 130.

The mobile device 130 is configured to receive the notification. In some examples, the mobile device 130 may display the notification on a display, such as the display of the mobile device 130. The mobile device 130 may be configured to obtain an indication to initiate the telehealth visit. The indication may be obtained via an input on the mobile device 130, such as a touch input or a voice input. In response to receiving the indication, the mobile device 130 may transmit a command to the server 110 to initiate the telehealth visit.

The server 110 is configured to receive the command and open a channel between the mobile device 120 and the mobile device 130. The channel may be configured as a real-time session channel to conduct the telehealth visit. The channel may be configured to support real-time audio and video communications.

To further illustrate an example use case for the mobile telehealth system 100, the following is provided. In an example, for the patient to be ready to be checked in, they will have had to complete the necessary fields in the medical and/or dental history, as well as have had entered a means of payment (or a code associated with a user type to bypass payment). The mobile device 120 may receive a pop-up notification reminding the patient to check into the virtual waiting room of the application. The patient, having checked into the waiting room, becomes visible to the healthcare provider via the mobile device 130. The mobile device 130 receives a notification that the patient, is in the virtual waiting room. The mobile telehealth system 100 may perform a matching of the patient name and appointment time. Both parties are alerted when they are a predetermined time (e.g., 10 minutes) from starting an appointment and are advised to be ready.

Figure 2:
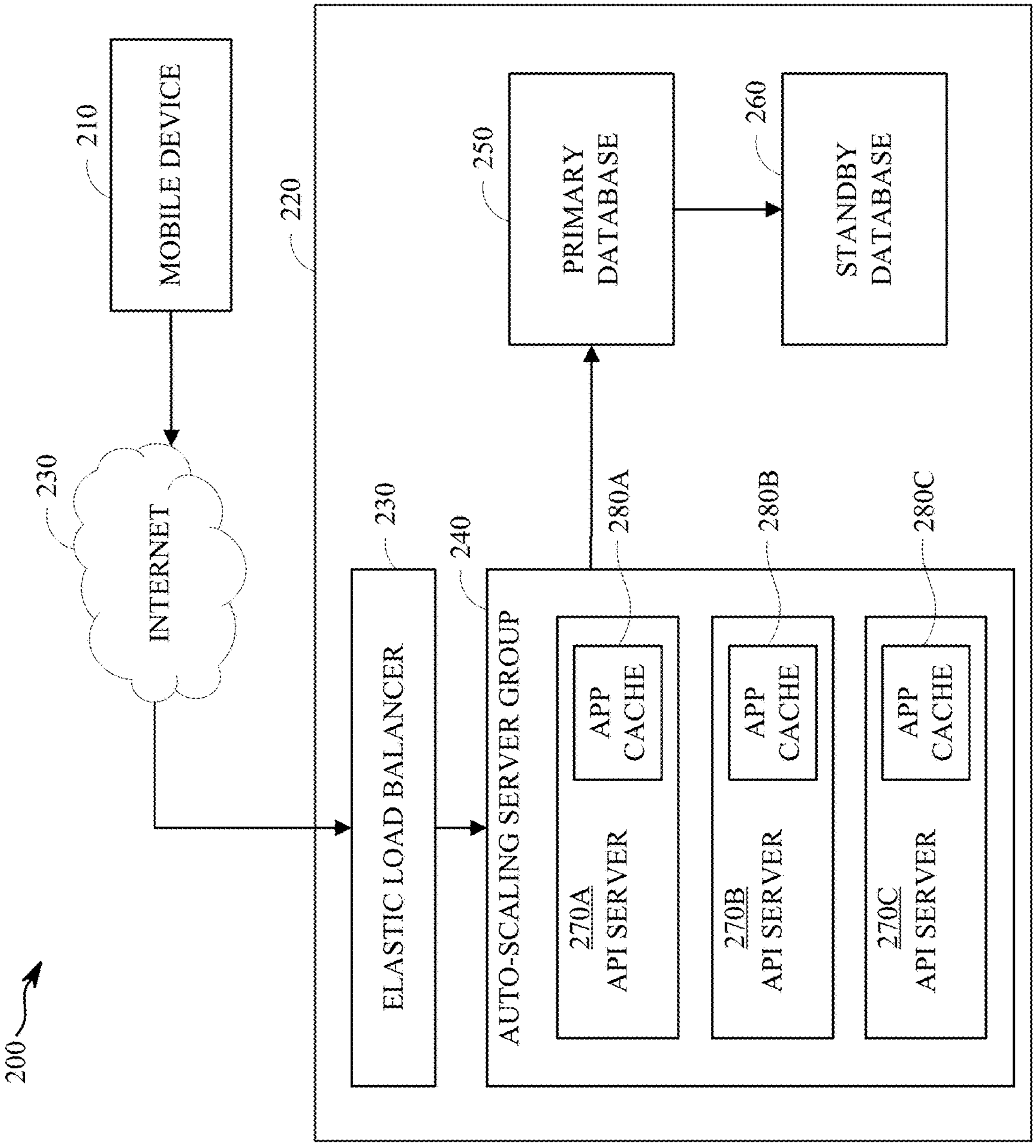
FIG. 2 is a block diagram of an example architecture of a mobile telehealth system.

FIG. 2 is a block diagram of an example architecture of a mobile telehealth system 200. The mobile telehealth system 200 includes at least one mobile device 210 and a datacenter 220 that are configured to communicate via the internet 230. In this example, the mobile device 210 may be any mobile device, such as mobile device 120 or mobile device 130 shown in FIG. 1. The mobile device 210 may be configured to run software based on a model-view-viewmodel (MVVM) architecture to reduce coupling, increase maintainability, or both.

As shown in FIG. 2, the datacenter 220 includes an elastic load balancer 230, an auto-scaling server group 240, a primary database 250, and a standby database 260. In an example, the server 110 shown in FIG. 1 may be the auto-scaling server group 240. The auto-scaling server group 240 is configured to support failover and includes one or more application programming interface (API) servers 270A-270C. The API servers 270A-270C are configured to auto-scale based on rules defined to increase the number of servers with a rise in communication traffic. The API servers 270A-270C are configured to have a near constant response time when the number of users is increasing. In an example, the API servers 270A-270C may be representational state transfer (REST) API servers configured to run Java Sprint Boot with spring security OAuth2. As shown in FIG. 2, each API server 270A-270C includes an application cache 280A-280C. In some examples, the application cache 280A-280C may be configured to store data such that the data is accessible without an internet connection.

The elastic load balancer 230 is configured to receive communication traffic from the at least one mobile device 210 via the internet 230. The elastic load balancer 230 is configured to route the communication traffic to the one or more API servers 270A-270C of the auto-scaling server group 240. The communication traffic may be routed based on a volume of the communication traffic.

The API servers 270A-270C are configured to perform automatic backups to the primary database 250. The automatic backups may be performed based on a predetermined schedule. If there is a failure at the primary database 250, the automatic backups may be failed over to the standby database 260. The primary database 250, the standby database 260, or both, may be PostgreSQL databases.

Figure 3:
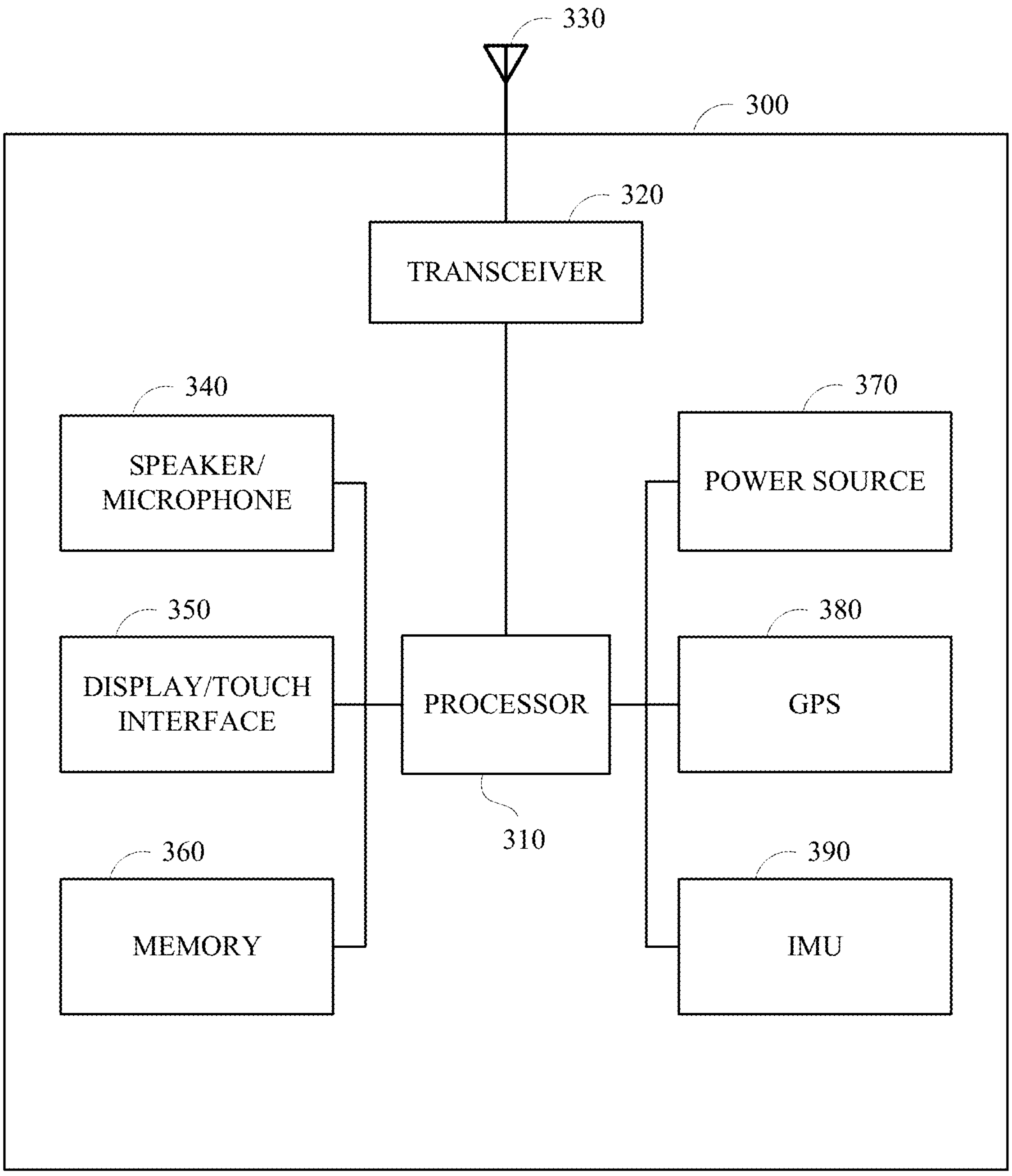
FIG. 3 is a block diagram of an example of a mobile device.

FIG. 3 is a diagram of an example of a mobile device 300. The mobile device 300 may be any mobile device, such as mobile device 120 or mobile device 130 shown in FIG. 1. The mobile device 300 may be a mobile phone, a smartphone, a tablet computing device, a laptop, or any other portable computing device. As shown in FIG. 3, the mobile device 300 includes a processor 310, a transceiver 320, an antenna 330, a speaker/microphone 340, a display/touch interface 350, memory 360, a power source 370, a global positioning system (GPS) chipset 380, and an inertial measurement unit (IMU) 390.

The processor 310 may be a general purpose processor, a special purpose processor, a conventional processor, a digital signal processor (DSP), one or more microprocessors, one or more microprocessors in association with a DSP core, a controller, a microcontroller, one or more Application Specific Integrated Circuits (ASICs), one or more Field Programmable Gate Array (FPGAs) circuits, any other type of integrated circuit (IC), a state machine, or any other processing device. The processor 310 may perform signal coding, data processing, power control, input/output processing, and/or any other functionality that enables the mobile device 300 to operate in a wireless environment. The processor 310 may be coupled to the transceiver 320, which may be coupled to the antenna 330. While FIG. 3 shows the processor 310 and the transceiver 320 as separate components, in some embodiments, the processor 310 and the transceiver 320 may be integrated together in an electronic package or chip. The processor 310 may be configured to execute instructions stored on a non-transitory computer readable medium, such as memory 360.

The transceiver 320 may be configured to modulate the signals that are to be transmitted by the antenna 330 and to demodulate the signals that are received by the antenna 330.

The antenna 330 may be configured to transmit signals and receive signals over an air interface. For example, the antenna 330 may be configured to transmit and/or receive radio frequency (RF) signals. In an embodiment, the antenna 330 may be an emitter/detector configured to transmit and/or receive infrared (IR), ultraviolet (UV), or visible light signals, for example. In yet an embodiment, the antenna 330 may be configured to transmit and receive both RF and light signals. It will be appreciated that the antenna 330 may be configured to transmit and/or receive any combination of wireless signals.

The processor 310 may be coupled to, and may receive user input data from, the speaker/microphone 340, the display/touch interface 350 (e.g., a liquid crystal display (LCD) display unit or organic light-emitting diode (OLED) display unit), or both. The processor 310 may also output user data to the speaker/microphone 340, the display/touch interface 350, or both. In addition, the processor 310 may access information from, and store data in, any type of suitable memory, such as the memory 360. The memory 360 may include random-access memory (RAM), read-only memory (ROM), a hard disk, a subscriber identity module (SIM) card, a memory stick, a secure digital (SD) memory card, or any other type of memory storage device. In an embodiment, the processor 310 may access information from, and store data in, memory that is not physically located on the mobile device 300, such as on the server 110 shown in FIG. 1 or a home computer (not shown).

The processor 310 may receive power from the power source 370, and may be configured to distribute and/or control the power to the other components of the mobile device 300. The power source 370 may be any suitable device for powering the mobile device 300. For example, the power source 370 may include one or more dry cell batteries (e.g., nickel-cadmium (NiCd), nickel-zinc (NiZn), nickel metal hydride (NiMH), lithium-ion (Li-ion)), solar cells, fuel cells, and the like.

The processor 310 may also be coupled to the GPS chipset 380, which may be configured to provide location information (e.g., longitude and latitude) regarding the current location of the mobile device 300. In addition to, or in lieu of, the information from the GPS chipset 380, the mobile device 300 may receive location information over the air interface and/or determine its location based on the timing of the signals being received from two or more nearby base stations. It will be appreciated that the mobile device 300 may acquire location information by way of any suitable location-determination method while remaining consistent with an embodiment.

The processor 310 may further be coupled to the IMU 390. The IMU 390 may be configured to measure and report a specific force of the mobile device 300, an angular rate of the mobile device 300, an orientation of the mobile device 300, or any combination thereof, using one or more of an accelerometer, a gyroscope, and a magnetometer.

Figure 4:
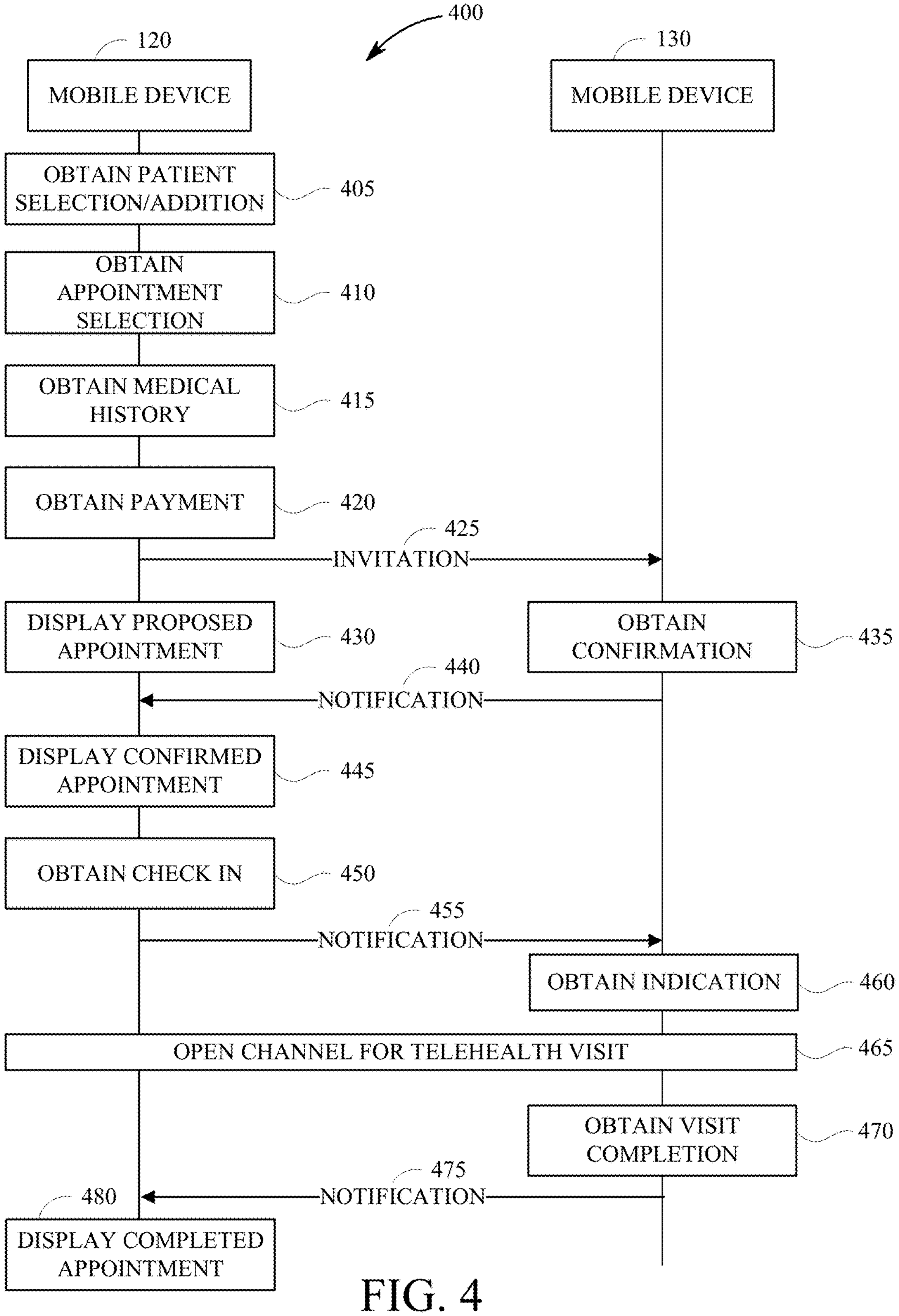
FIG. 4 is a diagram of an example of an appointment scheduling workflow.

FIG. 4 is a diagram of an example of an appointment scheduling workflow 400. The appointment scheduling workflow 400 is shown between mobile device 120 and mobile device 130 shown in FIG. 1. For simplicity and clarity, a server is not shown, however, it is understood that the communications between mobile device 120 and mobile device 130 are performed through a server, such as server 110 shown in FIG. 1.

In this example, the mobile device 120 may be a patient mobile device and the mobile device 130 may be a healthcare provider mobile device. In some examples, the mobile device 120 may be configured to communicate with one or more devices, such as devices that are configured for home medical and/or dental use. The mobile device 120 may be configured to obtain 405 an existing patient selection or addition of a new patient, for example, from a database. The selection or addition of a patient may be obtained via an input on the mobile device 120, such as a touch input or a voice input. The mobile device 120 may be configured to transmit the selection or addition of the patient to the server.

The mobile device 120 may be configured to query the server to obtain a list of available appointment slots in a schedule of the healthcare provider. The mobile device 120 may be configured to obtain 410 an appointment selection from the patient. The appointment selection may be obtained via an input on the mobile device 120, such as a touch input or a voice input. The appointment selection may be based on an available appointment slot in the schedule of the healthcare provider stored on the server. The mobile device 120 may be configured to transmit the appointment selection to the server. The server may receive the appointment selection and update the schedule of the healthcare provider to indicate that the selected appointment is tentative.

The mobile device 120 may be configured to obtain 415 a medical history of the patient. The medical history may be obtained via an input on the mobile device 120, such as a touch input or a voice input. The mobile device 120 may be configured to transmit the medical history to the server. In some embodiments, the mobile device 120 may be configured to upload one or more documents and/or images to the server 110. In some embodiments, the server may obtain 415 a medical history or a portion of a medical history from an EHR system, such as the EHR system 140 shown in FIG. 1.

The mobile device 120 is configured to obtain 420 payment information. The payment information may be transmitted to the server. The server may store the payment information. In an example, the server is configure to process the payment information and transmit an invitation 425 to the mobile device 130. In another example, the mobile device 120 is configured to transmit the invitation 425 to the mobile device 130 via the server. The invitation 425 may include information associated with the appointment, for example date, time, type of appointment, patient name, patient symptoms, and any other relevant patient information. The mobile device 120 may be configured to display 430 an indication of the proposed appointment on the display of the mobile device 120. The mobile device 130 is configured to obtain 435 a confirmation from the healthcare provider. The confirmation may be obtained via an input on the mobile device 130, such as a touch input or a voice input. The mobile device 130 may transmit a notification 440 to the mobile device 120 via the server. The notification 440 may indicate that the appointment is confirmed.

The mobile device 120 is configured to receive the notification 440 and display 445 an indication of the confirmed appointment on the display of the mobile device 120. The mobile device 120 is configured to obtain 450 a check in from the patient. The check in may indicate that the patient is ready to start the telehealth visit. The check in may be obtained via an input on the mobile device 120, such as a touch input or a voice input. The mobile device 120 may transmit a notification 455 to the mobile device 130 via the server in response to the input. The notification 445 may indicate that the patient is ready to start the telehealth visit.

The mobile device 130 is configured to receive the notification 455. In some examples, the mobile device 130 may display the notification 455 on a display, such as the display of the mobile device 130. The mobile device 130 may be configured to obtain 460 an indication to initiate the telehealth visit. The indication may be obtained via an input on the mobile device 130, such as a touch input or a voice input. In response to obtaining the indication, the mobile device 130 may transmit a command to the server to initiate the telehealth visit.

The server is configured to receive the command and open 465 a channel between the mobile device 120 and the mobile device 130. The channel may be configured as a real-time session channel to conduct the telehealth visit. The channel may be configured to support real-time audio and video communications.

The mobile device 130 is configured to perform image and/or video captures of the patient using a camera of the mobile device 120. The mobile device 120 may be configured to display alignment lines to guide the patient to properly align the mobile device 120 for the image and/or video capture. In some examples, the alignment lines may be displayed as dental arch overlays or facial feature overlays. In some examples, cartoon depictions of the pose may be displayed to guide the patient. In some examples, the cartoon depictions may include a text or audible description of the pose. The mobile device 120 is configured to scan the patient's face to detect whether proper alignment is achieved. Once proper alignment is achieved, the mobile device 120 performs the image and/or video capture. The mobile device 130 is configured to obtain input from the healthcare provider to annotate the image and/or video captures in real-time. The mobile device 120 may capture a series of images that can be used to determine a preliminary diagnosis. The preliminary diagnosis may be determined based on specific orientations or poses for images of a patient's face. For example, orienting a patient in a position such as full face, or straight profile, where the patient's eyes, nose, and mouth are parallel to the horizon, the system may determine an asymmetry value. The asymmetry value may be an integer value, and may be determined at the mobile device 120, the mobile device 130, or at a server of the system, such as server 110 shown in FIG. 1. The preliminary diagnosis may be based on a determination that the asymmetry value is above a threshold. The input may be a touch input, a text input, a voice input, or a combination thereof.

Upon completion of the telehealth visit, the mobile device 130 is configured to obtain 470 an indication of visit completion. The indication of visit completion may be obtained via an input on the mobile device 130. The input may include a touch input or a voice input. In response to obtaining the indication of visit completion, the mobile device 130 may transmit a notification 475 to the mobile device 120 via the server. The notification 475 may indicate that the appointment is completed. The mobile device 120 may be configured to display 480 the notification 475, for example, on a display of the mobile device 120.

Upon completion of, or during the telehealth visit, the mobile device 130 may be configured to provide the healthcare provider the ability to write an electronic prescription (e-prescription). The mobile device 130 may be configured to add appointment notes. The appointment notes may be added via text input, voice input, or any other suitable input. The appointment notes entry may be enhanced with spell-checking, particularly for industry or specialty specific terminology. The appointment notes entry may include pre-designed templates and one or more elements that are auto-filled with data from a memory. The mobile device 130 may be configured to save the image and/or video captures, for example, with or without annotations. The images, video captures, and/or annotations may be saved in the appointment notes portion of an electronic file associated with the patient. The mobile device 130 may be configured to mark the appointment as completed. The mobile device 130 may be configured to automatically send a post-visit summary to the patient, for example, via email, short messaging service (SMS) text, or some other method.

Upon completion of the telehealth visit, the mobile device 130 may be configured to access an e-prescription. The mobile device 120 may be configured to view the appointment notes. The mobile device 120 may be configured to view the image and/or video captures, for example, with or without annotations. An example annotation of an image may include a circle drawn around, or an arrow pointing to, an area of concern on the image, such as a decaying or broken tooth. The mobile device 120 may be configured to receive the post-visit summary, for example, via email, SMS text, or some other method.

Figure 5:
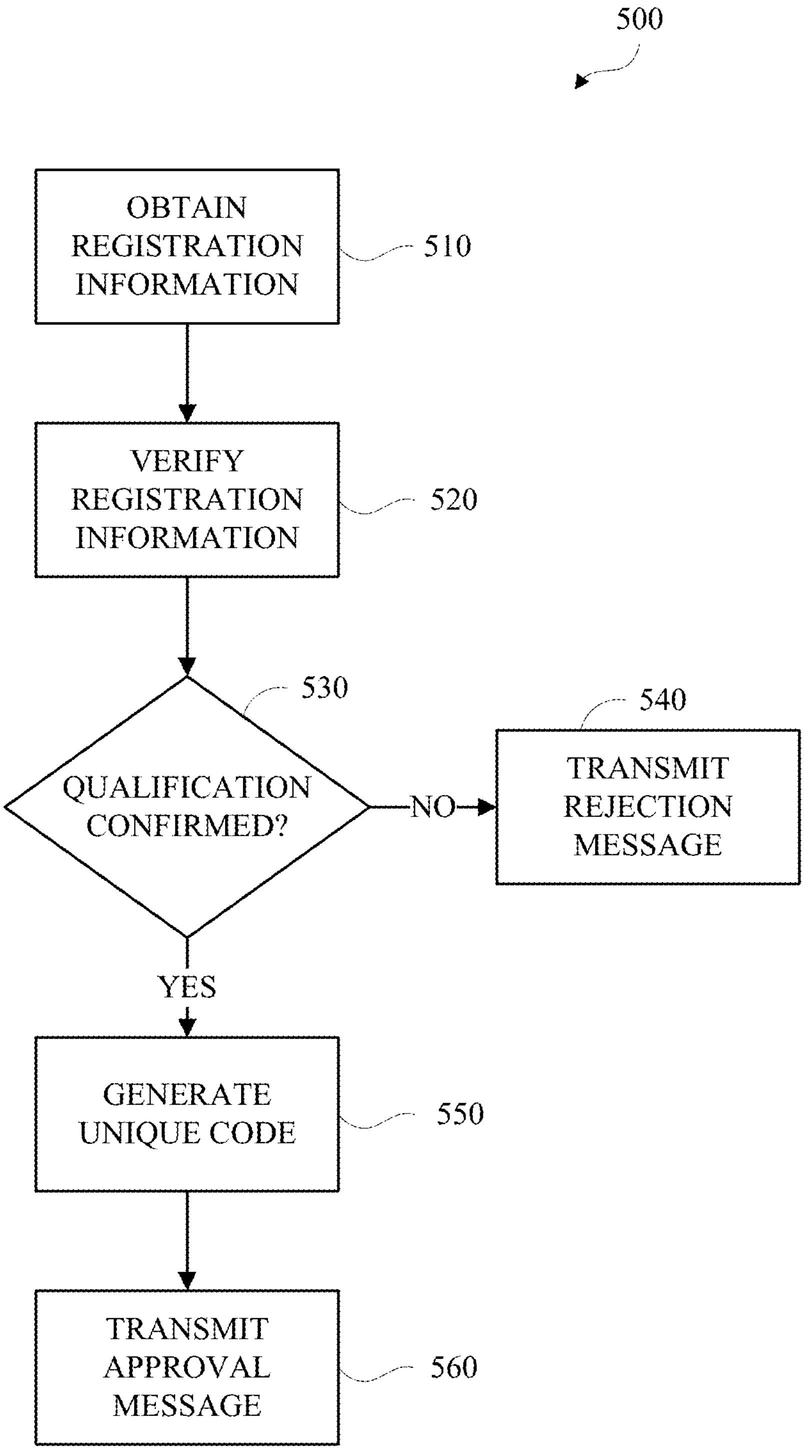
FIG. 5 is a flow diagram of an example of a healthcare provider qualification method.

FIG. 5 is a flow diagram of an example of a healthcare provider qualification method 500. The method 500 includes obtaining 510 registration information. The obtained registration information may be transmitted to a server, such as server 110 shown in FIG. 1, for processing. The registration information may be obtained via any computing device, such as, for example, mobile device 130 shown in FIGS. 1 and 4. The registration information may include educational experience, such as degrees and specialty certificates earned, residency programs completed, or any combination thereof. The registration information may include state licensing verification, practice history, experience, patient reviews, or any combination thereof. The registration information may include disciplinary matters, including, for example, medical malpractice claims. The registration information may include hospital privileges, whether granted, denied, or revoked. In an example, the registration may include the first and last name of the physician, email address, phone number, type of implementation, name of practice, location of practice, website, individual national provider identifier (NPI), practice NPI, professional license number, state, and renewal date, or any combination thereof. The type of implementation may be chosen from a dropdown menu and may include a standard free download and a premium download that includes an e-prescribing feature.

The method 500 includes automatically verifying 520 the registration information. In response to verifying the registration information, the method 500 includes determining 530 whether the healthcare provider is qualified. The determination of the qualification of the healthcare provider is based on the automatic verification of the registration information. For example, if one or more elements of the obtained registration information (or some other threshold) cannot be verified, the healthcare provider may be deemed unqualified. If it is determined that the healthcare provider is not qualified, the method 500 includes transmitting 540 a rejection message to the computing device. The rejection message may be transmitted as an email, an SMS text, or some other communication. The determination of the qualification of the healthcare provider may be performed using a third party software service.

If it is determined that the healthcare provider is qualified, the method 500 includes generating 550 a unique code. The unique code is associated with the healthcare provider. The unique code may be a one-time use code that expires after a predetermined time if it goes unused. The method 500 includes transmitting 560 an approval message to the computing device. The approval message may be transmitted as an email, an SMS text, or some other communication. The approval message may include the unique code. The unique code may be displayed on a display of the computing device. The unique code may be entered into the system via the computing device to authenticate and associate the computing device of the healthcare provider with the system.

Figure 6:
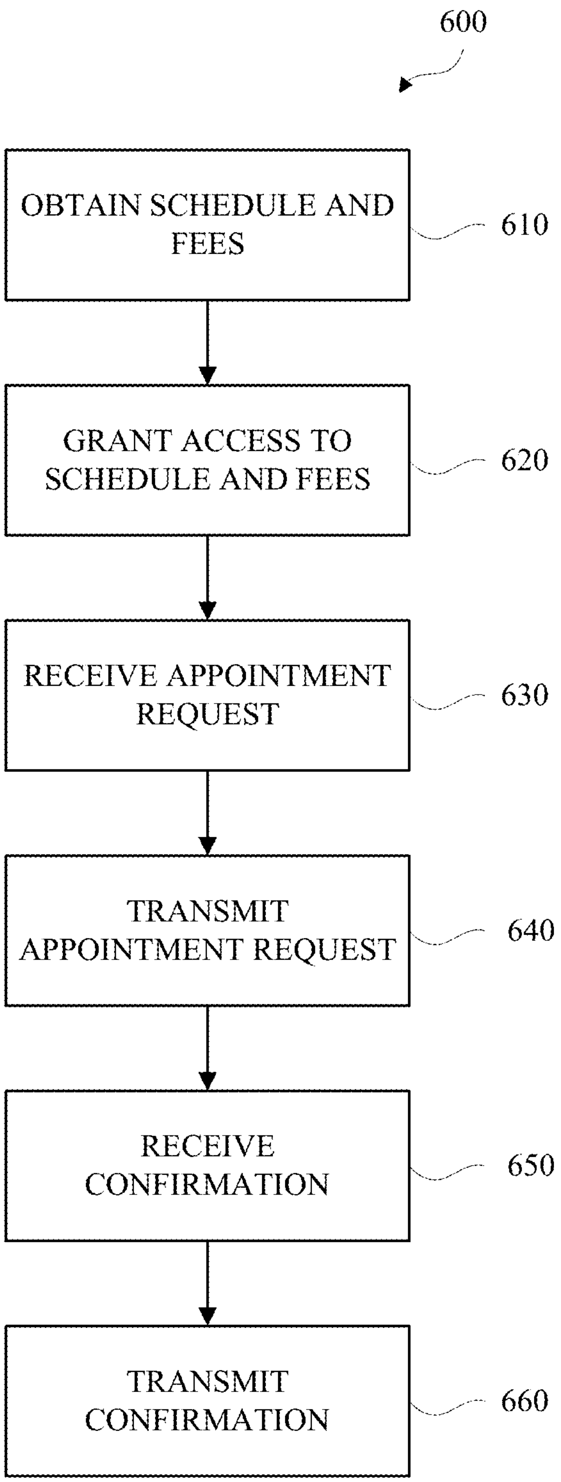
FIG. 6 is a flow diagram of an example of a method for scheduling an appointment.

FIG. 6 is a flow diagram of an example of a method 600 for scheduling an appointment. The method 600 includes obtaining 610 a schedule and fees from a healthcare provider. The healthcare provider schedule and fees may be obtained via an input on a computing device, such as computing device 130 shown in FIGS. 1 and 4. The input may be a touch input, a text input, or a voice input. In an example, the healthcare provider may indicate their availability to see patients via the input.

The method 600 includes granting 620 access to the schedule and fees. The granting of access may be based on a role assigned to the registered user of the system. For example, a user with a role "patient" may have access to the schedule and fees. Once access is granted, the patient may view the schedule and fees on a computing device, such as mobile device 120 shown in FIGS. 1 and 4.

The method 600 includes receiving 630 a request for an appointment, for example, from the mobile device 120, and transmitting 640 the appointment request, for example, to the mobile device 130. If the healthcare provider accepts the appointment request, the method 600 includes receiving 650 a confirmation from the mobile device 130 and transmitting 660 the confirmation to the mobile device 120.

Figure 7:
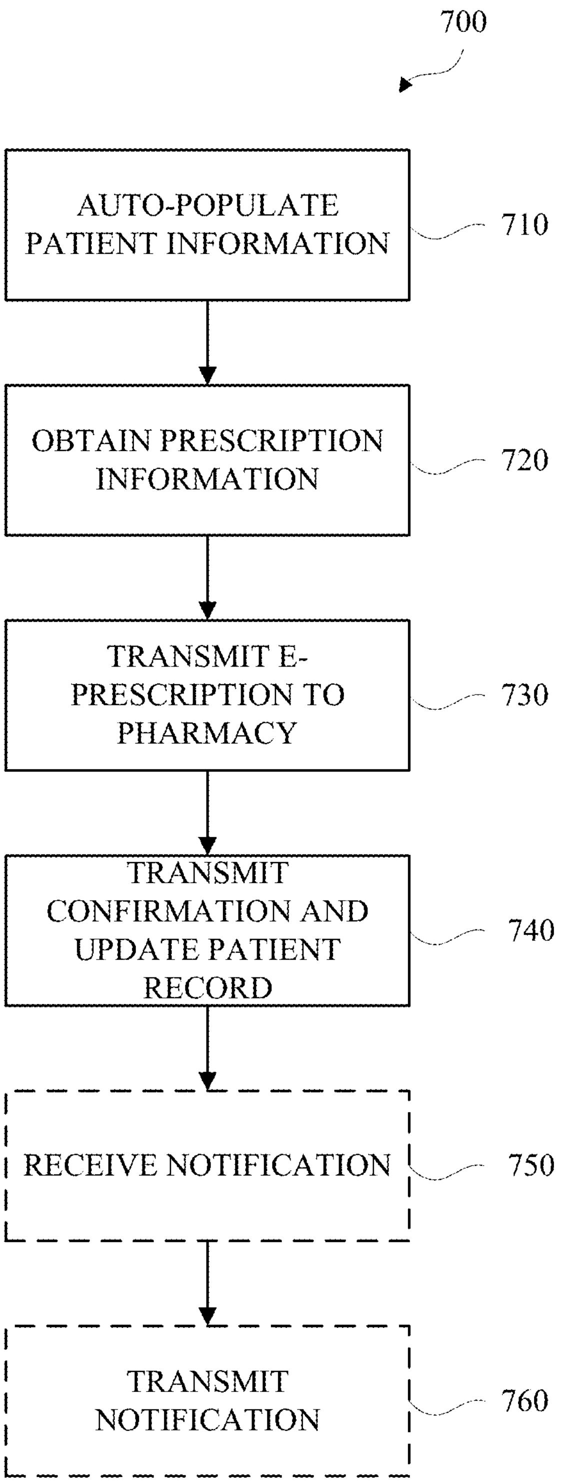
FIG. 7 is a flow diagram of an example of a method for electronic prescription.

FIG. 7 is a flow diagram of an example of a method 700 for electronic prescription (e-prescription). The method 700 includes auto-populating 710 patient information to generate an e-prescription. The patient information may be obtained from a server, such as server 110 shown in FIG. 1. The patient information may include the first and last name of the patient, patient identification number, preferred pharmacy, or any combination thereof. The method includes obtaining 720 prescription information from the healthcare provider. The prescription information includes the name of the prescribed medication, dosage, number of refills, special instructions, or any combination thereof. The patient information and the prescription information may be combined to generate the e-prescription.

The method 700 includes transmitting 730 the e-prescription to a pharmacy or a third party service, for example, the preferred pharmacy indicated in the patient information. The e-prescription may be transmitted via email, SMS text, or any other suitable communication. The method 700 includes transmitting 740 a confirmation and updating the patient record to include the prescribed medication. The confirmation may indicate that the e-prescription has been sent to the pharmacy. The confirmation may be transmitted to the patient device, the healthcare provider device, or both. In some embodiments, the method 700 may include receiving 750 a notification from the pharmacy that the prescription is ready for pick up, and transmitting 760 the notification to the patient device.

Figure 8:
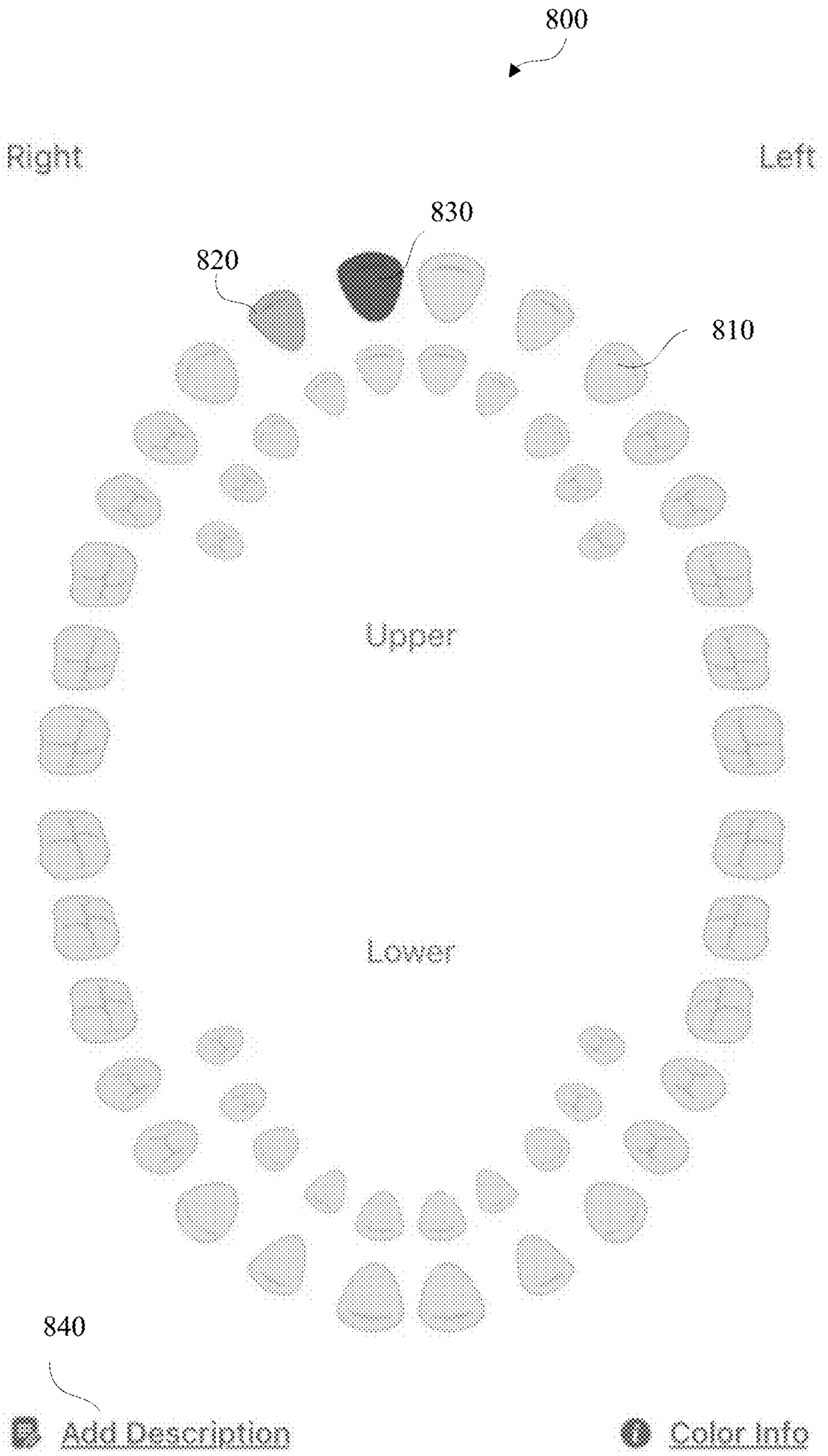
FIG. 8 is a diagram of a universal dentition chart in accordance with embodiments of this disclosure.

FIG. 8 is a diagram of a universal dentition chart 800 in accordance with embodiments of this disclosure. As shown in FIG. 8, the universal dentition chart 800 includes a visual representation of a patient's teeth. The visual representation is universal and does not require a numbering system. In an example, the visual representation may be an illustration of the maxillary and mandibular dental arches, as viewed from the top down. The teeth may be shown in their approximate proper location within the dental arch. The physician can identify the teeth individually by the visual representation, and will not require a numbering system for orientation, thereby making this charting system universally recognizable, i.e., by both domestic and foreign dentists, and dentists of different specialties that may have differing nomenclatures for identification of individual teeth. The visual representation can show a tooth that is not present 810, a tooth that is present 820, and a tooth that indicates a pathology 830. The tooth pathology can be noted 840 and notations can be made. The tooth pathology may be linked to particular teeth individually, if desired.

Figure 9:
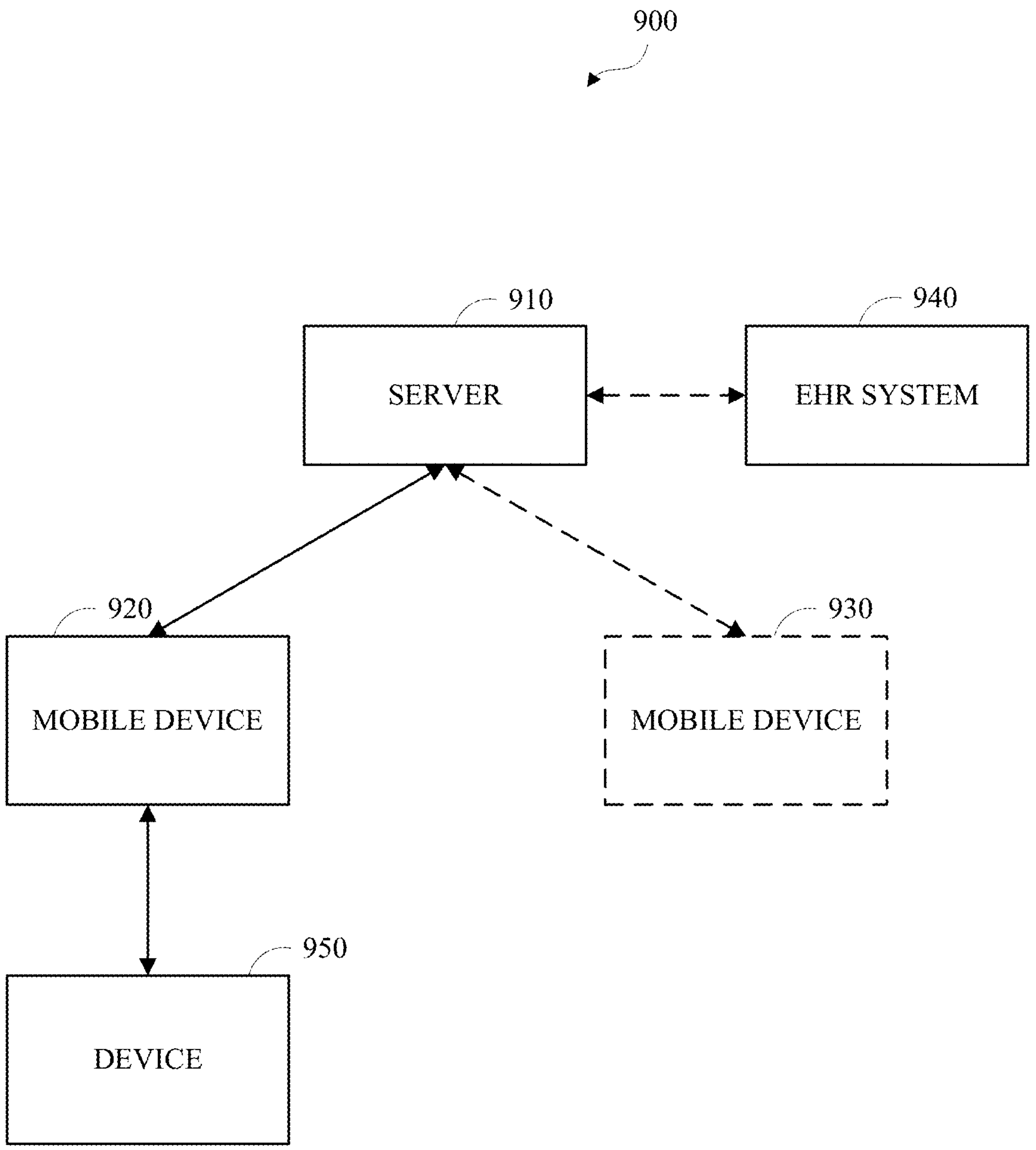
FIG. 9 is a diagram of an example of the mobile telehealth system shown in FIG. 1.

FIG. 9 is a diagram of an example of the mobile telehealth system shown in FIG. 1. As shown in FIG. 9, the mobile telehealth system 900 includes a server 910, a mobile device 920, a mobile device 930, an EHR system 940, and a device 950.

The server 910 may be a computer hardware device or software that provides functionality for other programs or devices known as clients. The clients may be mobile devices such as mobile device 920 and mobile device 930. In some examples, the EHR system 940 may be a client. The server 910 may provide services, such as sharing data or resources among multiple clients and devices. The server 910 may perform computations for a client.

In this example, the mobile device 920 may be a patient mobile device and the mobile device 930 may be a healthcare provider mobile device. As shown in FIG. 9, the mobile device 920 is configured to communicate with device 950. The mobile device 920 may be configured to communicate with device 950 via a wired or wireless link. For example, the mobile device 920 may communicate with device 950 via Bluetooth, WiFi, ZigBee, near-field communications (NFC), ultra-wideband communications (UWC), or any other suitable wireless technology.

The device 950 may be a portable healthcare device, for example, configured for home use by a patient. The device 950 may be part of a home diagnostic testing kit. The device 950 may include interchangeable parts that perform different functions. For example, an interchangeable part may include a camera that is configured to scan a body part of a patient, such as a face or other body part. In an example, the scanned body part may be used to determine an asymmetry that indicates swelling. An interchangeable part may include a camera that is configured to scan an internal portion of a patient body, such as a mouth or ear. An interchangeable part may include a light sensor to detect ambient light, for example, when scanning for tooth shade to filter the ambient light from the scan to improve accuracy. In an example, the interchangeable part may include one or more sensors configured to scan for tooth shade, detect tooth decay, detect gum disease, determine a dental arch, or any combination thereof. In an example, the one or more sensors may include a spectrophotometer to determine a tooth shade. The spectrophotometer may be configured to perform measurements in a range of approximately 400 nm to approximately 700 nm to determine the tooth shade. Determining a dental arch may include generating a two-dimensional or three-dimensional image from multiple image scans. The two-dimensional or three-dimensional images may be mapped to data points in a digital patient chart, and the digital patient chart may be updated to include these images. The determined dental arch may be interactive such that it can be viewed from multiple angles. The one or more sensors may include a camera, an infrared (IR) detector, an ultraviolet (UV) detector, a spectrophotometric detector, a laser detector, a temperature detector, an inertial measurement unit (IMU), or any combination thereof.

The device 950 is configured to obtain data from the one or more sensors and transmit the data to the mobile device 920. The mobile device 920 is configured to determine tooth shade, detect tooth decay, determine gum disease, determine a dental arch, or any combination thereof, using one or more artificial intelligence (AI) algorithms. The mobile device 920 may be configured to determine whether the device 950 is in the correct position based on the sensor data. If it is determined that the device 950 is not in the correct position, the mobile device 920 may determine instructions to correct the position, and display or transmit the instructions. The instructions may include audible and/or haptic feedback that cause the device 950 to emit an audible alert or vibration. In some examples, the mobile device 920 may transmit the data to the server 910, and the server 910 may be configured to determine tooth shade, detect tooth decay, determine gum disease, determine a dental arch, or any combination thereof, using one or more AI algorithms. In an example, the server 910, the mobile device 920, or both, may be configured to generate a timeline for display on the mobile device 920. The timeline may be generated to so a change in tooth shade over time, a change in tooth decay over time, a change in gum health over time, or any combination thereof. In some examples, the server 910, the mobile device 920, or both, may be configured to generate a prediction of a change in tooth shade over time, a change in tooth decay over time, a change in gum health over time, or any combination thereof.

The prediction may be based on the effectiveness of a commercial product or prescription product. The prediction may take into account patient medical data in order to determine the prediction.

The mobile device 920, the mobile device 930, or both, may be configured to obtain a medical history of the patient. The term "medical history" as used herein may include dental history. In some examples, the medical history may be obtained by transmitting a request to the server 910. The request may include an instruction to retrieve the medical history or a digital patient chart from the EHR system 940. In some examples, the medical history may be obtained via an input on the mobile device 920, such as a touch input or a voice input. The mobile device 920 may be configured to transmit the medical history to the server 910. In some embodiments, the mobile device 920 may be configured to upload one or more documents and/or images to the server 910. In some embodiments, the server may obtain a medical history or a portion of a medical history from the EHR system 940. The EHR system 140 is associated with the healthcare provider. The EHR system 140 is configured to store electronic health records of patients of the healthcare provider. The EHR system 140 may be configured to generate, store, and update a digital patient chart. The digital patient chart may be generated based on the medical history. In some examples, the server 910 may be configured to generate the digital patient chart and transmit the digital patient chart to the EHR system 940 for storage. The digital patient chart is an electronic file that includes health data associated with a given patient. The health data may include text, diagrams, images, audio, video, or any combination thereof. The EHR system 940 may be configured to transmit the digital patient chart to the server 910, which may transmit the digital patient chart to the mobile device 920, mobile device 930, or both, for display. The EHR system 940 may be located on premises at the office of the healthcare provider, or it may be at a remote location away from the healthcare provider office. In an example, the server 910 may obtain an EHR from the EHR system 940. The server 910 may be configured to receive the medical history or portions of the medical history from the mobile device 920 and the EHR system 940, compile the medical history, and transform the compiled medical history into a unified format. The unified format of the medical history may be stored on the server 910.

Figure 10:
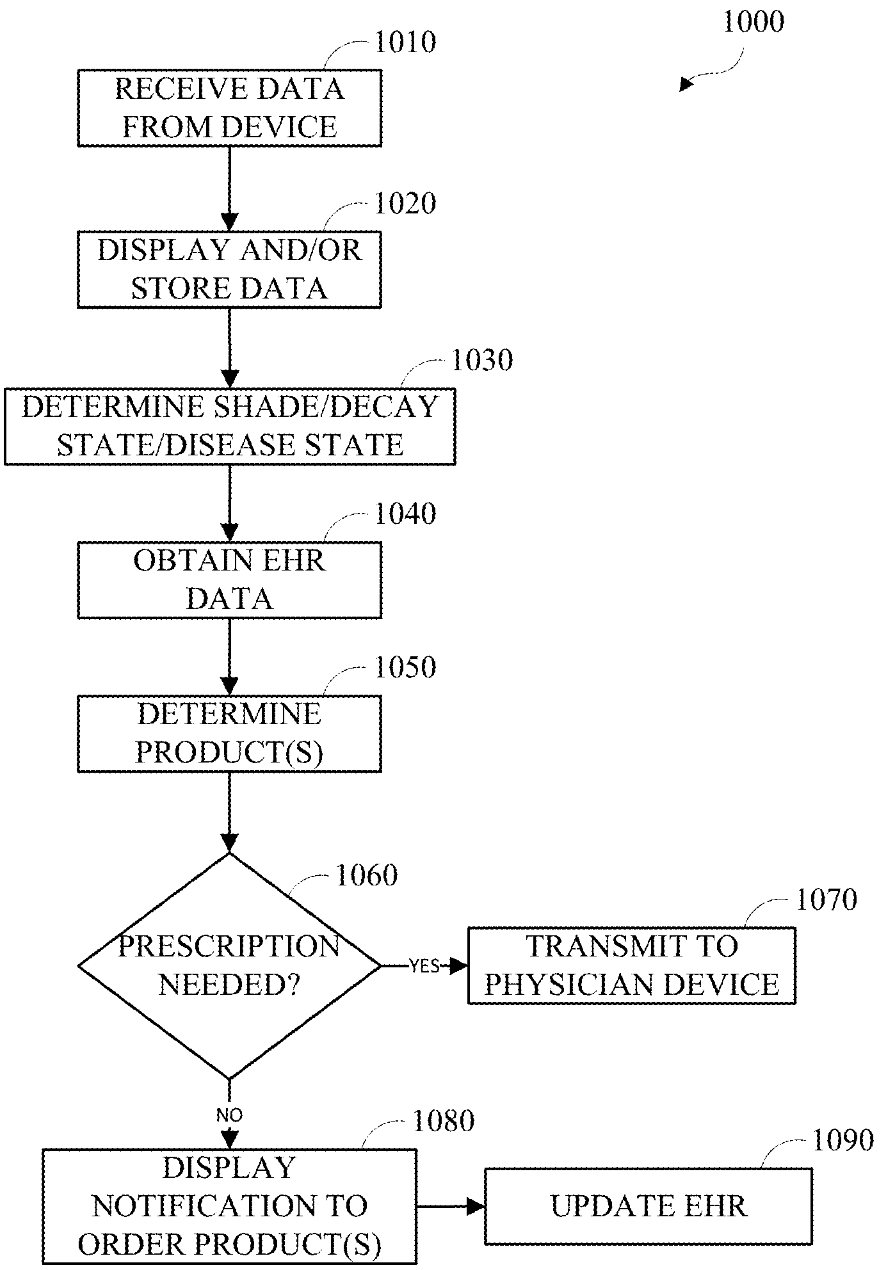
FIG. 10 is a flow diagram of an example of a method for home healthcare access.

FIG. 10 is a flow diagram of an example of a method 1000 for home healthcare access. At 1010, the method 1000 includes receiving data from a device, for example, device 950 shown in FIG. 9. The data may include image data, temperature data, inertial measurement unit (IMU) data, infrared (IR) data, and ultraviolet (UV) data, spectrophotometric data, or any combination thereof. At 1020, the method 1000 includes displaying and/or storing the data. The data may include image data that is displayed on a display, for example, a display of the mobile device 920 shown in FIG. 9. In an example, the data may be stored in a memory of the mobile device 920 or transmitted to the server 910 for further processing or storage. Displaying the data may include verifying a specific tooth or location in the patient's mouth so that it is associated with a corresponding tooth or location on a dental record, and displaying when the tooth or location is verified. One or more AI algorithms may be used to verify the specific tooth or location. The one or more AI algorithms may be used to automatically map each tooth or location using captured images to generate a dental chart. The one or more AI algorithms may be used to guide the patient to the correct tooth or location to enable the patient to perform a self-scan. In an example, the patient may be guided to a particular tooth that was subject to a previous root canal. The guidance may be provided via audio and/or haptic feedback. In another example, the patient may provide a voice input, such as "What tooth is this?" and receive an audible or text response from the mobile device 920 or the device 950 in response to the voice input.

At 1030, the method 1000 includes determining a tooth shade, a decay state, a disease state, or any combination thereof. The determining may include processing the obtained data, such as spectrophotometric data, using one or more AI algorithms and/or a neural network, such as a convolutional neural network (CNN), for example. The determining may include verifying a specific tooth so that it is associated with a corresponding tooth on a dental record. In a tooth shade example, the determining may include filtering out an ambient noise signal from the obtained data. At 1040, the method may include obtaining EHR data. The EHR data may be used to determine a decay state or a disease state.

At 1050, the method 1000 includes determining one or more products. The one or more products may be determined based on the determined tooth shade, decay state, disease state, or any combination thereof. The one or more products may be determined based on the EHR data. For example, the EHR data may include allergy information of the patient, the method is configured to eliminate products to which the patient is may be allergic. The one or more products may include tooth straightening products, tooth whitening products, antibiotics, fluoride products, analgesics, or any combination thereof. The tooth whitening products may include dental trays, tooth whitening gels, tooth whitening strips, or the like. Determining the one or more products may include displaying a visual comparison of the effectiveness of each product based on the patient data. One or more AI algorithms may be used to determine a level of tooth color lightening that may be possible based on the patient's existing tooth color as determined by the shade detecting device, such as device 950. The visual comparison can be used by the patient to determine which product is best for them. For example, the achievable tooth color lightening levels for each product may be displayed on a display of the mobile device 920 such that the patient is enabled to select the product according to their preference.

At 1060, the method 1000 includes determining whether a prescription for the one or more products is needed. This step may include referencing a look up table (LUT) to determine whether a prescription is needed. If it is determined that a prescription is needed, the method 1000 includes transmitting 1070 a notification to a physician device, such as mobile device 930 shown in FIG. 9. The notification may be transmitted via a server, such as server 910 shown in FIG. 9. The notification may be displayed on the physician device and enable the physician to approve or deny the prescription.

If a prescription is not needed, the method 1000 includes displaying 1080 a notification to order the one or more products. If it is determined that a product is ordered, the EHR may be updated at 1090 to indicate the ordered product. If it is determined that a product is ordered, the method 1000 may arrange for purchase and delivery of the product.

In some examples, the method may include monitoring the scans at prescribed times and documenting the progress until the patient achieves a desired result.

As used herein, the terminology "computer" or "computing device" includes any unit, or combination of units, capable of performing any method, or any portion or portions thereof, disclosed herein.

As used herein, the terminology "processor" indicates one or more processors, such as one or more special purpose processors, one or more digital signal processors, one or more microprocessors, one or more controllers, one or more microcontrollers, one or more application processors, one or more central processing units (CPU)s, one or more graphics processing units (GPU)s, one or more digital signal processors (DSP)s, one or more application specific integrated circuits (ASIC)s, one or more application specific standard products, one or more field programmable gate arrays, any other type or combination of integrated circuits, one or more state machines, cloud-based computing processors, or any combination thereof.

As used herein, the terminology "memory" indicates any non-transitory computer-usable or computer-readable medium or device that can tangibly contain, store, communicate, or transport any signal or information that may be used by or in connection with any processor. For example, a memory may be one or more read only memories (ROM), one or more random access memories (RAM), one or more registers, low power double data rate (LPDDR) memories, one or more cache memories, one or more semiconductor memory devices, one or more magnetic media, one or more optical media, one or more magneto-optical media, or any combination thereof.

As used herein, the terminology "instructions" may include directions or expressions for performing any method, or any portion or portions thereof, disclosed herein, and may be realized in hardware, software, cloud-based computing environment(s), or any combination thereof. For example, instructions may be implemented as information, such as a computer program, stored in memory that may be executed by a processor to perform any of the respective methods, algorithms, aspects, or combinations thereof, as described herein. Instructions, or a portion thereof, may be implemented as a special purpose processor, or circuitry, that may include specialized hardware for carrying out any of the methods, algorithms, aspects, or combinations thereof, as described herein. In some implementations, portions of the instructions may be distributed across multiple processors on a single device, on multiple devices, which may communicate directly or across a network such as a local area network, a wide area network, the Internet, or a combination thereof.

As used herein, the terminology "determine" and "identify," or any variations thereof, includes selecting, ascertaining, computing, looking up, receiving, determining, establishing, obtaining, or otherwise identifying or determining in any manner whatsoever using one or more of the devices and methods shown and described herein.

As used herein, the terminology "example," "embodiment," "implementation," "aspect," "feature," or "element" indicates serving as an example, instance, or illustration. Unless expressly indicated, any example, embodiment, implementation, aspect, feature, or element is independent of each other example, embodiment, implementation, aspect, feature, or element and may be used in combination with any other example, embodiment, implementation, aspect, feature, or element.

As used herein, the terminology "or" is intended to mean an inclusive "or" rather than an exclusive "or." That is, unless specified otherwise, or clear from context, "X includes A or B" is intended to indicate any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from the context to be directed to a singular form.

Further, for simplicity of explanation, although the figures and descriptions herein may include sequences or series of steps or stages, elements of the methods disclosed herein may occur in various orders or concurrently. Additionally, elements of the methods disclosed herein may occur with other elements not explicitly presented and described herein. Furthermore, not all elements of the methods described herein may be required to implement a method in accordance with this disclosure. Although aspects, features, and elements are described herein in particular combinations, each aspect, feature, or element may be used independently or in various combinations with or without other aspects, features, and elements.

What is claimed is:

1. A method comprising:

obtaining, via a user interface of a first mobile device, a patient selection;

obtaining, via the user interface of the first mobile device, an appointment selection;

obtaining, via the user interface of the first mobile device, a medical history;

obtaining, via the user interface of the first mobile device, payment information;

in response to obtaining the payment information, transmitting an invitation to a second mobile device;

receiving a first notification from the second mobile device;

obtaining, via the user interface of the first mobile device, a check in;

in response to obtaining the check in, transmitting a second notification to the second mobile device;

obtaining a channel between the first mobile device and the second mobile device, wherein the channel is a real-time session channel to conduct a telehealth visit;

transforming the medical history into a unified format comprising a labeled map comprising an annotated representation of a patient's teeth;

providing a portable healthcare device comprising a scanning camera, an ambient light sensor, at least one sensor configured to detect a dental condition, and a spectrophotometric detector;

wherein the first mobile device is configured to display a plurality of anatomical alignment lines to guide a patient in properly positioning the scanning camera to capture a plurality of images;

sending the plurality of images to the second mobile device; and updating the labeled map with the plurality of images; and wherein the first mobile device is configured to provide a haptic feedback.

2. The method of claim 1, wherein the first mobile device is associated with a patient.

3. The method of claim 1, wherein the second mobile device is associated with a healthcare provider.

4. The method of claim 1 further comprising:

obtaining, via a user interface of the second mobile device, a confirmation.

5. The method of claim 4, wherein the first notification is transmitted in response to obtaining the confirmation.

6. The method of claim 4, wherein the confirmation indicates that an appointment is confirmed.

7. The method of claim 6 further comprising:

displaying, on a display of the first mobile device, the confirmation.

8. The method of claim 1 further comprising:

obtaining, via a user interface of the second mobile device, an indication of visit completion.

9. The method of claim 8 further comprising:

transmitting a third notification in response to obtaining the indication of visit completion.

10. The method of claim 9 further comprising:

displaying, on a display of the first mobile device, the third notification.

* * * * *